(12) United States Patent
Palti et al.

(10) Patent No.: US 11,701,161 B2
(45) Date of Patent: *Jul. 18, 2023

(54) OPTIMIZING TREATMENT USING TTFIELDS BY CHANGING THE FREQUENCY DURING THE COURSE OF LONG TERM TUMOR TREATMENT

(71) Applicant: Novocure GmbH, Root (CH)

(72) Inventors: Yoram Palti, Haifa (IL); Matan Dishon, Kibbutz Mizra (IL)

(73) Assignee: Novocure GmbH, Root (CH)

( * ) Notice: Subject to any disclaimer, the term of this patent is extended or adjusted under 35 U.S.C. 154(b) by 362 days.

This patent is subject to a terminal disclaimer.

(21) Appl. No.: 17/023,990

(22) Filed: Sep. 17, 2020

(65) Prior Publication Data

US 2021/0000528 A1 Jan. 7, 2021

Related U.S. Application Data

(63) Continuation of application No. 15/493,309, filed on Apr. 21, 2017, now Pat. No. 10,779,875, which is a (Continued)

(51) Int. Cl.
*A61B 18/12* (2006.01)
*A61B 5/0536* (2021.01)
(Continued)

(52) U.S. Cl.
CPC ............ *A61B 18/12* (2013.01); *A61B 5/0536* (2013.01); *A61B 18/1206* (2013.01);
(Continued)

(58) Field of Classification Search
CPC ...... A61B 18/1206; A61B 2018/00732; A61B 2018/00875; A61B 2018/147

See application file for complete search history.

(56) References Cited

U.S. PATENT DOCUMENTS 5,369,014 A 11/1994 Brugnara et al.
6,238,342 B1 5/2001 Feleppa et al.
(Continued)

FOREIGN PATENT DOCUMENTS

JP 2001276008 A 10/2001
WO 2010107715 A1 9/2010

OTHER PUBLICATIONS

International Search Report and Written Opinion for International Application No. PCT/IB2014/000688 dated Oct. 15, 2014.
(Continued)

*Primary Examiner* — Daniel W Fowler
(74) *Attorney, Agent, or Firm* — Potomac Law Group, PLLC

(57) ABSTRACT

Tumors can be treated with an alternating electric field. The size of cells in the tumor is determined prior to the start of treatment by, for example, biopsy or by inverse electric impedance tomography. A treatment frequency is chosen based on the determined cell size. The cell size can be determined during the course of treatment and the treatment frequency is adjusted to reflect changes in the cell size. A suitable apparatus for this purpose includes a device for measuring the tumor impedance, an AC signal generator with a controllable output frequency, a processor for estimating the size of tumor cells and setting the frequency of the AC signal generator based thereon, and at least one pair of electrodes operatively connected to the AC signal generator such that an alternating electric field is applied to the tumor.

5 Claims, 10 Drawing Sheets

Related U.S. Application Data continuation-in-part of application No. 14/269,784, filed on May 5, 2014, now Pat. No. 9,655,669.

(60) Provisional application No. 61/819,717, filed on May 6, 2013.

(51) Int. Cl.
*A61B 90/00* (2016.01)
*A61B 18/00* (2006.01)
*A61B 18/14* (2006.01)

(52) U.S. Cl.
CPC .... *A61B 90/37* (2016.02); *A61B 2018/00732* (2013.01); *A61B 2018/00875* (2013.01); *A61B 2018/124* (2013.01); *A61B 2018/128* (2013.01); *A61B 2018/147* (2013.01); *A61B 2090/374* (2016.02); *A61B 2090/3762* (2016.02); *A61B 2576/00* (2013.01)

(56) References Cited

U.S. PATENT DOCUMENTS

| | | | |
|---|---|---|---|
| 6,868,289 B2 | 3/2005 | Palti | |
| 7,016,725 B2 | 3/2006 | Palti | |
| 7,089,054 B2 | 8/2006 | Palti | |
| 7,136,699 B2 | 11/2006 | Palti | |
| 7,146,210 B2 | 12/2006 | Palti | |
| 7,333,852 B2 | 2/2008 | Palti | |
| 7,467,011 B2 | 12/2008 | Palti | |
| 7,519,420 B2 | 4/2009 | Palti | |
| 7,565,205 B2 | 7/2009 | Palti | |
| 7,565,206 B2 | 7/2009 | Palti | |
| 7,599,745 B2 | 10/2009 | Palti | |
| 7,599,746 B2 | 10/2009 | Palti | |
| 7,706,890 B2 | 4/2010 | Palti | |
| 7,715,921 B2 | 5/2010 | Palti | |
| 7,805,201 B2 | 9/2010 | Palti | |
| 7,890,183 B2 | 2/2011 | Palti et al. | |
| 7,912,540 B2 | 3/2011 | Palti | |
| 7,917,227 B2 | 3/2011 | Palti | |
| 8,019,414 B2 | 9/2011 | Palti | |
| 8,027,738 B2 | 9/2011 | Palti | |
| 8,170,684 B2 | 5/2012 | Palti | |
| 8,175,698 B2 | 5/2012 | Palti et al. | |
| 8,229,555 B2 | 7/2012 | Palti | |
| RE43,618 E | 8/2012 | Palti | |
| 8,244,345 B2 | 8/2012 | Palti | |
| 8,406,870 B2 | 3/2013 | Palti | |
| 8,447,395 B2 | 5/2013 | Palti et al. | |
| 8,447,396 B2 | 5/2013 | Palti et al. | |
| 8,465,533 B2 | 6/2013 | Palti | |
| 8,706,261 B2 | 4/2014 | Palti | |
| 8,715,203 B2 | 5/2014 | Palti | |
| 8,718,756 B2 | 5/2014 | Palti | |
| 8,764,675 B2 | 7/2014 | Palti | |
| 9,023,090 B2 | 5/2015 | Palti | |
| 9,023,091 B2 | 5/2015 | Palti | |
| 9,039,674 B2 | 5/2015 | Palti et al. | |
| 9,056,203 B2 | 6/2015 | Palti et al. | |
| 9,440,068 B2 | 9/2016 | Palti et al. | |
| 9,655,669 B2 | 5/2017 | Palti et al. | |
| 9,750,934 B2 | 9/2017 | Palti et al. | |
| 10,188,851 B2 | 1/2019 | Wenger et al. | |
| 10,441,776 B2 | 10/2019 | Kirson et al. | |
| 10,779,875 B2 | 9/2020 | Palti et al. | |
| 10,821,283 B2 | 11/2020 | Giladi et al. | |
| 2002/0042609 A1 | 4/2002 | Kelman et al. | |
| 2002/0072742 A1 | 6/2002 | Schaefer et al. | |
| 2003/0105411 A1 | 6/2003 | Smallwood et al. | |
| 2004/0147984 A1 | 7/2004 | Altshuler et al. | |
| 2006/0015095 A1 | 1/2006 | Desinger et al. | |
| 2006/0167499 A1 | 7/2006 | Palti | |
| 2006/0282122 A1 | 12/2006 | Palti | |
| 2006/0293731 A1* | 12/2006 | Rubinsky | A61B 18/1477 607/98 |
| 2007/0033660 A1 | 2/2007 | Palti | |
| 2007/0225766 A1 | 9/2007 | Palti | |
| 2007/0239213 A1 | 10/2007 | Palti | |
| 2008/0287944 A1 | 11/2008 | Pearson et al. | |
| 2009/0076366 A1 | 3/2009 | Palti | |
| 2010/0023004 A1* | 1/2010 | Francischelli | A61B 18/1492 606/41 |
| 2010/0049077 A1 | 2/2010 | Sadleir et al. | |
| 2010/0121173 A1 | 5/2010 | Sarfaty et al. | |
| 2011/0137229 A1 | 6/2011 | Palti et al. | |
| 2011/0212029 A1 | 9/2011 | Bayford et al. | |
| 2012/0157989 A1 | 6/2012 | Stone et al. | |
| 2012/0197243 A1 | 8/2012 | Sherman et al. | |
| 2012/0283726 A1 | 11/2012 | Palti | |
| 2013/0178819 A1 | 7/2013 | Palti et al. | |
| 2013/0178820 A1 | 7/2013 | Palti et al. | |
| 2013/0184637 A1 | 7/2013 | Palti | |
| 2013/0184674 A1 | 7/2013 | Palti | |
| 2014/0330268 A1 | 11/2014 | Palti et al. | |
| 2017/0120041 A1 | 5/2017 | Wenger et al. | |
| 2017/0215939 A1 | 8/2017 | Palti et al. | |
| 2017/0281934 A1 | 10/2017 | Giladi et al. | |
| 2018/0001075 A1 | 1/2018 | Kirson et al. | |
| 2018/0008708 A1 | 1/2018 | Giladi et al. | |
| 2018/0050200 A1 | 2/2018 | Wasserman et al. | |
| 2018/0160933 A1 | 6/2018 | Urman et al. | |
| 2018/0202991 A1 | 7/2018 | Giladi et al. | |
| 2019/0117956 A1 | 4/2019 | Wenger et al. | |
| 2019/0117963 A1 | 4/2019 | Travers et al. | |
| 2019/0307781 A1 | 10/2019 | Krex et al. | |
| 2019/0308016 A1 | 10/2019 | Wenger et al. | |
| 2020/0001069 A1 | 1/2020 | Kirson et al. | |
| 2020/0009376 A1 | 1/2020 | Chang et al. | |
| 2020/0009377 A1 | 1/2020 | Chang et al. | |
| 2020/0016067 A1 | 1/2020 | Gotlib et al. | |
| 2020/0023179 A1 | 1/2020 | Bomzon et al. | |
| 2020/0061360 A1 | 2/2020 | Hagemann et al. | |
| 2020/0061361 A1 | 2/2020 | Hagemann et al. | |
| 2020/0069937 A1 | 3/2020 | Naveh et al. | |
| 2020/0078582 A1 | 3/2020 | Alon et al. | |
| 2020/0108031 A1 | 4/2020 | Borst et al. | |
| 2020/0121728 A1 | 4/2020 | Wardak et al. | |
| 2020/0129761 A1 | 4/2020 | Bomzon et al. | |
| 2020/0146586 A1 | 5/2020 | Naveh et al. | |
| 2020/0155835 A1 | 5/2020 | Wasserman et al. | |
| 2020/0171297 A1 | 6/2020 | Kirson et al. | |
| 2020/0179512 A1 | 6/2020 | Giladi et al. | |
| 2020/0219261 A1 | 7/2020 | Shamir et al. | |
| 2020/0254242 A1 | 8/2020 | Chang et al. | |
| 2020/0269037 A1 | 8/2020 | Hagemann et al. | |
| 2020/0269041 A1 | 8/2020 | Zeevi et al. | |
| 2020/0269042 A1 | 8/2020 | Giladi et al. | |
| 2020/0269043 A1 | 8/2020 | Wasserman et al. | |
| 2020/0306531 A1 | 10/2020 | Tran et al. | |
| 2020/0330755 A1 | 10/2020 | Wasserman et al. | |
| 2020/0368525 A1 | 11/2020 | Maag et al. | |

OTHER PUBLICATIONS

Kirson et al., "Alternating electric fields arrest cell proliferation in animal tumor models and human brain tumors," PNAS, vol. 104, No. 24, Jun. 12, 2007.
Extended European Search Report issued in application No. EP20217359 dated Apr. 23, 2021.
Qiao et al., "Bioimpedance Analysis for the Characterization of Breast Cancer Cells in Suspension," IEEE Transactions on Biomedical Engineering, vol. 59, No. 8, pp. 2321-2329, Aug. 2012.
Gimsa et al.., "A Unified Resistor-Capacitor Model for Impedance, Dielectrophoresis, Electrorotation, and Induced Transmembrane Potential," Biophysical Journal, vol. 75, pp. 1107-1116, Aug. 1998.
Kirson et al., "Disruption of Cancer Cell Replication by Alternating Electric Fields," Cancer Research, vol. 64, pp. 3288-3295, May 2004.

* cited by examiner

| | | |
|---|---|---|
| e0 | 8.85e-12[F/m] | free space permittivity |
| Vtot | 1[V] | total voltage applied |
| d | 5[um] | diameter of the cell |
| gap | 50 [nm] | gap between cells |
| g | gap/2 | |
| a | d+2*g | length of block |
| rhoExt | 200[ohm*cm] | Extracellular resistivity |
| rhoMem | 10e6 [ohm*cm] | Membrane resistivity |
| rhoInt | 500[ohm*cm] | Intracellular resistivity |
| ereExt | 60 | extracellular relative permittivity |
| ereMem | 9.04 | membrane relative permittivity |
| ereInt | 60 | intracellular relative permittivity |
| dMem | 8[nm] | membrane thickness |
| CpAMem | eMem/dMem | membrane capacitance |
| RpAMem | dMem/sMem | membrane conductance |
| sExt | 1/rhoExt | extracellular conductivity |
| sMem | 1/rhoMem | membrane conductivity |
| sInt | 1/rhoInt | intracellular conductivity |
| eMem | e0*ereMem | membrane permittivity |

Table 1

FIG. 13

OPTIMIZING TREATMENT USING TTFIELDS BY CHANGING THE FREQUENCY DURING THE COURSE OF LONG TERM TUMOR TREATMENT

CROSS-REFERENCE TO RELATED APPLICATION

This application is a continuation of U.S. application Ser. No. 15/493,309, filed Apr. 21, 2017, which is a continuation-in-part of U.S. application Ser. No. 14/269,784, filed May 5, 2014, which claims priority to and the benefit of U.S. provisional application 61/819,717, filed May 6, 2013. Each of the above-identified applications is incorporated herein by reference in its entirety.

FIELD OF THE INVENTION

The present invention relates, generally, to systems and methods for optimizing the frequency of electromagnetic radiation used in the long term treatment of tumors.

BACKGROUND OF THE INVENTION

Living organisms proliferate by cell division, including tissues, cell cultures, microorganisms (such as bacteria, mycoplasma, yeast, protozoa, and other single-celled organisms), fungi, algae, plant cells, etc. When in the process of dividing, cells of organisms can be destroyed, or their proliferation controlled, by methods that are based on the sensitivity of the dividing cells of these organisms to certain chemical or physical agents.

It is well known that tumors, particularly malignant or cancerous tumors, grow uncontrollably compared to normal tissue. Such expedited growth enables tumors to occupy an ever-increasing space and to damage or destroy tissues and organs adjacent thereto. Furthermore, certain cancers are characterized by an ability to spread metastases to new locations where the metastatic cancer cells grow into additional tumors.

The rapid growth of tumors, in general, and malignant tumors in particular, as described above, is the result of relatively frequent cell division of these cells compared to normal tissue cells. The distinguishably frequent cell division of cancer cells is the basis for the effectiveness of many existing cancer treatments, e.g., irradiation therapy and the use of various chemo-therapeutic agents. Such treatments are based on the fact that cells undergoing division are more sensitive to radiation and chemo-therapeutic agents than non-dividing cells. Because tumor cells divide much more frequently than normal cells, it is possible, to a certain extent, to selectively damage or destroy tumor cells by radiation therapy and/or chemotherapy. The actual sensitivity of cells to radiation, therapeutic agents, etc., is also dependent on specific characteristics of different types of normal or malignant cells. Unfortunately, in many cases the sensitivity of tumor cells to the applied therapeutic agent is not sufficiently higher than that of many types of normal tissues, therefore existing cancer treatments typically cause significant damage to normal tissues, thus limiting the therapeutic effectiveness of such treatments. Also, certain types of tumors are not sensitive at all to existing methods of treatment.

Electric fields and currents have been used for medical purposes for many years. The most common use is the generation of electric currents in a human or animal body by application of an electric field by means of a pair of conductive electrodes between which a potential difference is maintained. These electric currents are used either to exert their specific effects, i.e., to stimulate excitable tissue, or to generate heat by flowing in the body since it acts as a resistor. Examples of the first type of application include the following: cardiac defibrillators, peripheral nerve and muscle stimulators, brain stimulators, etc. Currents are used for heating, for example, in devices for tumor ablation, ablation of malfunctioning cardiac or brain tissue, cauterization, relaxation of muscle rheumatic pain and other pain, etc.

Another use of electric fields for medical purposes involves the utilization of high frequency oscillating fields transmitted from a source that emits an electric wave, such as an RF wave or a microwave source, which is directed at the part of the body that is of interest (i.e., a target).

Historically, electric fields used in medical applications were separated into two types, namely (1) steady fields or fields that change at relatively slow rates, and alternating fields of low frequencies that induce corresponding electric currents in the body or tissues, and (2) high frequency alternating fields (above 1 MHz) applied to the body by means of the conducting electrodes or by means of insulated electrodes.

The first type of electric field has been used, for example, to stimulate nerves and muscles, pace the heart, etc. In fact, such fields are used in nature to propagate signals in nerve and muscle fibers, the central nervous system (CNS), heart, etc. The recording of such natural fields is the basis for the ECG, EEG, EMG, ERG, etc. The field strength in a medium having uniform electric properties is simply the voltage applied to the stimulating/recording electrodes divided by the distance between them. The currents thus generated can be calculated by Ohm's law. Those currents, however, can have dangerous stimulatory effects on the heart and CNS and can result in potentially harmful ion concentration changes. Also, if the currents are strong enough, they can cause excessive heating in the tissues. This heating can be calculated by the power dissipated in the tissue (the product of the voltage and the current).

When such electric fields and currents are alternating, their stimulatory power (e.g., on nerve, muscle, etc.) is an inverse function of the frequency. At frequencies above 10 kHz, the stimulation power of the field approaches zero. This limitation is due to the fact that excitation induced by electric stimulation is normally mediated by membrane potential changes, the rate of which is limited by the resistive and capacitive properties (with time constants on the order of 1 ms) of the membrane.

Regardless of the frequency, when such current inducing fields are applied, they are often associated with harmful side effects caused by currents. For example, one negative effect is the change in ionic concentration in the various "compartments" within the system, and the harmful products of the electrolysis.

Historically, alternating fields of medium frequencies (about 50 kHz-1 MHz) were thought not to have any biological effect except due to heating. But more recently, the usefulness of such fields has been recognized, particularly when the fields are applied to a conductive medium, such as a human body, via insulated electrodes. Under such conditions the electrodes induce capacitive currents in the body. In U.S. Pat. Nos. 7,016,725, 7,089,054, 7,333,852, 7,805,201, and 8,244,345 by Palti (each of which is incorporated herein by reference) and in a publication by Kirson (see Eilon D. Kirson, et al., Disruption of Cancer Cell Replication by Alternating Electric Fields, Cancer Res. 2004

64:3288-3295), such fields have been shown to have the capability to specifically affect cancer cells and serve, among other uses, for treating cancer. These fields are referred to herein as TTFields.

The above listed references demonstrate that the efficacy of alternating fields in specifically damaging cancer cells is frequency dependent, and also demonstrate that the optimal frequency is different for different cell types. Thus for example the optimal frequency for malignant melanoma tumor cells is 100 kHz, while that for Glioblastoma multiforme is 200 kHz. It was further demonstrated that these differences result from the differences in cell size as shown in another publication by Kirson (see Kirson E D, Dbaly V, Tovarys F, et al. Alternating electric fields arrest cell proliferation in animal tumor models and human brain tumors. Proc Natl Acad Sci U.S.A. 2007; 104:10152-10157). Thus for each type of cancer, treatment is preferably given at a particular optimal frequency.

The frequency used for the treatment is based on the inverse relationship between the cell size and the optimal treatment frequency as calculated by Kirson (see Kirson E D, Dbaly V, Tovarys F, et al. Alternating electric fields arrest cell proliferation in animal tumor models and human brain tumors. Proc Natl Acad Sci USA. 2007; 104:10152-10157) on the basis of the maximal electric force exerted on the polar particles in the dividing tumor cell (during cytokinesis) is depicted in FIG. 1. Note that the experimentally determined optimal treatment frequency and histological measurements of cell size in melanoma and glioma fall reasonably well on the calculated curve.

One shortcoming of previous approaches as described above, is the use of a single fixed frequency throughout the treatment of a tumor. While the frequency may be optimal at the start of the treatment, previous approaches did not take into account the possibility that the cells in the tumor may change size as the treatment progresses. Thus, previous approaches failed to optimize the frequency of radiation directed at the tumor throughout the treatment process.

SUMMARY OF THE INVENTION

The embodiments described herein provide a second-order improvement to the Palti and Kirson advances, based on the inventor's recognition that during the course of treatment for a particular type of cancer, the average cell size may not remain constant. As a result, the efficacy of the treatment may be improved by optimizing the frequency over time during the treatment to match expected changes in the cell size that occur over time.

An apparatus and related method for optimizing cancer treatment with TTFields are provided. Optimization is achieved by adjusting the frequency of the alternating electric field to the value that is clinically optimal for the specific tumor in the individual patient at different times during the course of treatment. The basis of the method is the fact that the maximal exerted force on cell components by electric field forces including dielectrophoresis forces is both cell size and frequency dependent. As a result there is an optimal treatment frequency that is dependent on the specific tumor cell size at any given moment in time. Moreover, since the cell size changes over time, the frequency should be changed to compensate for the changes in the cell size to maintain the most effective treatment.

In one aspect, the invention features a method for adaptively treating a tumor with an alternating electric field. The method involves applying an alternating electric field having a first frequency to the tumor. The method further involves determining an impedance of the tumor based on a measured current while the alternating electric field having the first frequency is applied. Additionally, the method involves estimating a size of cells in the tumor based on the determined impedance. The method also involves selecting a second frequency based on the estimated size of cells. Thus, determination of the impedance leads to selection of the treatment frequency. Moreover, the method involves applying an alternating electric field to the tumor at the second frequency to treat the tumor.

In some embodiments, the method involves waiting for a period of time. The method further involves applying an alternating electric field having a third frequency to the tumor. The method further involves determining a second impedance of the tumor based on a measured current while the alternating electric field having the third frequency is applied. The method further involves estimating a second size of cells in the tumor based on the determined second impedance. The method further involves selecting a fourth frequency based on the estimated second size of cells. The method further involves applying an alternating electric field to the tumor at the fourth frequency to treat the tumor.

In some embodiments, the method further involves waiting for a period of at least one week. In some embodiments, the method further involves determining a size, shape, type, or location of the tumor. In some embodiments, the method further involves estimation of the size of cells based on a Cole-Cole plot. In some embodiments, the method further involves imaging the tumor with CT, MM, or PET to locate portions of the tumor not having excess blood or cyst fluid and estimating the size of cells based on a measured impedance of the located portions.

In another aspect, the invention relates to an apparatus for adaptively treating a tumor with electromagnetic radiation. The apparatus includes an electrical impedance tomography device for measuring the impedance of the tumor, the electrical impedance tomography device using a frequency such that a size of cells in the tumor can be determined from the measured impedance of the tumor. The apparatus also includes an AC signal generator having a controllable output frequency. The apparatus also includes a processor for estimating the size of cells in the tumor based on the measured impedance of the tumor and setting the frequency of the AC signal generator based on the estimated size of cells in the tumor. The apparatus also at least one pair of electrodes operatively connected to the AC signal generator such that an alternating electric field is applied to the tumor to selectively destroy cells in the tumor.

In some embodiments, the size of cells in the tumor is determined based on a Cole-Cole plot. In some embodiments, the apparatus further includes a CT, MRI, or PET imaging device configured to locate portions of the tumor not having excess blood or cyst fluid; and wherein the electrical impedance tomography device only measures the impedance of the located portions. In some embodiments, the electrical impedance tomography device is configured to make periodic impedance measurements. In some embodiments, the periodicity of the impedance measurements is at least one week. In some embodiments, the periodicity of the impedance measurements is at least one month. In some embodiments, the periodicity of the impedance measurements is based on a history of the tumor. In some embodiments, the periodicity of the impedance measurements is based on the type of tumor. In some embodiments, the frequency of the AC signal generator is set based on a spectrum of cell sizes. In some embodiments, the frequency of the AC signal generator is set based on an average cell size. In some embodiments, the processor computes a size of cells in the tumor based on a database look-up table.

In yet another aspect, the invention relates to a method for adaptively treating a tumor with an alternating electric field. The method involves determining a first size of cells in the tumor. The method also involves selecting a first frequency based on the determined first size. The method also involves applying an alternating electric field to the tumor at the first frequency to treat the tumor. The method also involves waiting a period of time and subsequently determining a second size of cells in the tumor. The method also involves selecting a second frequency based on the determined second size. The method also involves applying an alternating electric field to the tumor at the second frequency to treat the tumor.

In some embodiments, the method further involves the first size and the second size being determined based on a tumor biopsy. In some embodiments, the method further involves the first size and the second size being determined based on a measured impedance of the tumor. In some embodiments, the method further involves the determinations of the first size and the second size being made based on a Cole-Cole plot. In some embodiments, the method further involves imaging the tumor with CT, MRI, or PET to locate portions of the tumor not having excess blood or cyst fluid and determining the first size and the second size based on a measure impedance of the located portions. In some embodiments, the method further involves wherein the tumor is a glioma tumor or a melanoma tumor. In some embodiments, the method further involves wherein the period of time is at least one week. In some embodiments, the method further involves wherein the period of time is at least one month. In some embodiments, the method further involves wherein the first frequency and the second frequency are selected based on an average cell size. In some embodiments, the method further involves wherein the first frequency and the second frequency are selected based on a spectrum of cell sizes. In some embodiments, the method further involves wherein the period of time is chosen based on the type of tumor. In some embodiments, the method further involves wherein the period of time is chosen based on the history of the tumor. In some embodiments, the method further involves wherein the first size and the second size are determined based on a database look-up table.

In yet another aspect, the invention relates to a method for adaptively providing a medical treatment to a patient. The method involves applying an alternating electric field to a group of patient cells. The method also involves determining an impedance of the group of patient cells based on a measured current while the alternating electric field is applied. The method also involves selecting a treatment parameter based on the determined impedance. The method also involves applying a treatment to the patient in accordance with the selected treatment parameter.

In some embodiments, the method further involves waiting for a period of time. The method further involves applying an alternating electric field to a group of patient cells. The method further involves determining a second impedance of the group of patient cells based on a measured current while the alternating electric field is applied. The method further involves selecting a second treatment parameter based on the determined second impedance. The method further involves applying a treatment to the patient in accordance with the selected second treatment parameter.

In some embodiments, the method further involves estimating a size of cells in the group of patient cells based on the determined impedance or the determined second impedance. The method further involves selecting a treatment parameter based on the estimated size of cells. In some embodiments, the medical treatment is chemotherapy. In some embodiments, the medical treatment is a surgery or therapy. In some embodiments, the therapy is acoustic therapy, pharmacotherapy, radiation therapy, or nutritional therapy.

Yet another aspect of the invention is directed to a first apparatus for adaptively treating a tumor with an alternating electric field. The first apparatus comprises an AC signal generator, at least one pair of electrodes, an electrical impedance tomography device, and a processor. The AC signal generator has an output. The at least one pair of electrodes is operatively connected to the output of the AC signal generator such that an alternating electric field is applied to the tumor to selectively destroy cells in the tumor, and the AC signal generator is configured to apply a first alternating electrical signal to the output for a first period of time. The electrical impedance tomography device measures an impedance of the tumor to account for expected changes that occur as a result of treating the tumor for the first period of time. The processor is configured to adjust a parameter of treatment based on the measured impedance of the tumor after the first period of time, and further configured to account for changes in the tumor that have occurred during the first period of time by controlling the AC signal generator so that the AC signal generator applies a second alternating electrical signal to the output for a second period of time using the adjusted parameter of treatment. The second period of time is subsequent to the first period of time.

In some embodiments of the first apparatus, the parameter of treatment is an operating frequency of the AC signal generator. In some embodiments of the first apparatus, the first alternating electrical signal has a first frequency, and wherein the second alternating electric signal has a second frequency that is different from the first frequency. In some embodiments of the first apparatus, the AC signal generator and the electrical impedance tomography device are separate devices.

Another aspect of the invention is directed to a first method for adaptively treating a tumor with an alternating electric field. The first method comprises applying a first alternating electric field to the tumor for a first period of time to selectively destroy cells in the tumor; and measuring an impedance of the tumor to account for expected changes that occur as a result of treating the tumor for the first period of time. The first method also comprises adjusting a parameter of treatment based on the measured impedance of the tumor after the first period of time to account for changes in the tumor that have occurred during the first period of time; and applying a second alternating electric field to the tumor for a second period of time to selectively destroy cells in the tumor, wherein the second alternating electric field uses the adjusted parameter of treatment. The second period of time is subsequent to the first period of time.

In some instances of the first method, the parameter of treatment is an operating frequency. In some instances of the first method, the first alternating electrical field has a first frequency, and the second alternating electric field has a second frequency that is different from the first frequency.

BRIEF DESCRIPTION OF THE DRAWINGS

The advantages of the invention described above, together with further advantages, may be better understood by referring to the following description taken in conjunction with the accompanying drawings. The drawings are not necessarily to scale, emphasis instead generally being placed upon illustrating the principles of the invention.

FIG. 13 is a table of parameters used in the calculations shown in FIGS. 7-9.

DESCRIPTION OF THE PREFERRED EMBODIMENTS

In preferred embodiments of the invention, the size of cells in a tumor is determined throughout a treatment process utilizing TTFields. The frequency of the TTFields is then optimized based on the determined cell size. One way to determine the cell size (step 1120 in FIG. 11) is to first take impedance measurements, and then use those impedance measurements to compute the cell size. The tumor impedance can be determined, for example, by in-vivo MRI electrical impedance tomography (MREIT), or by following a new tumor impedance estimation method which may be termed "Inverse Electric Impedance Tomography" that is carried out as follows:

At the initial stage of the impedance estimation a CT, MRI, PET, or equivalent body/tissue imaging is made of the patient's tumor within its natural surrounding area. This image serves to determine the tumor location, size, shape, etc. relative to specific body markers.

Figure 3:
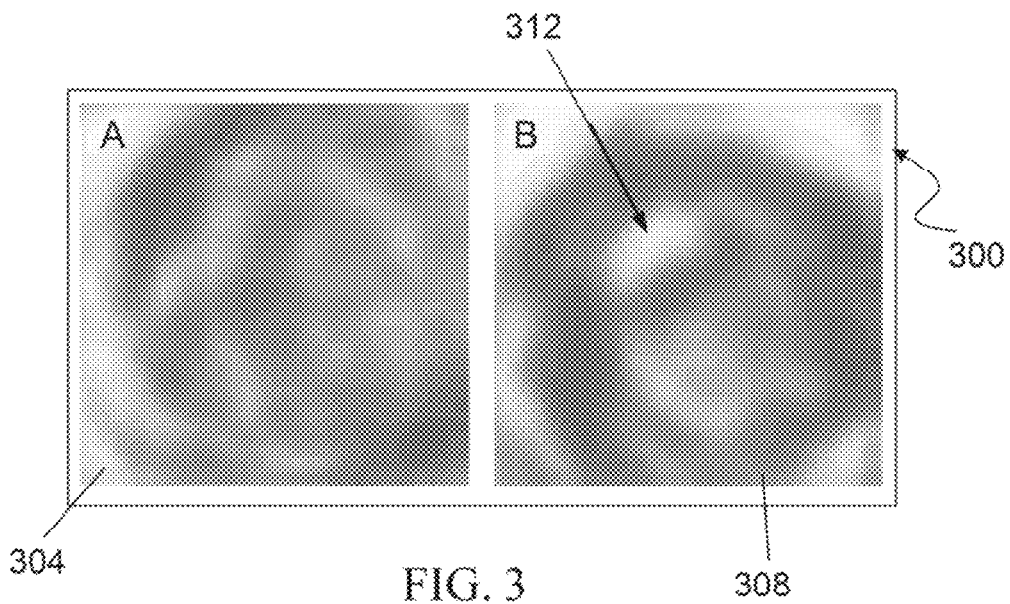
FIG. 3 is an image showing a normal breast and a breast with a tumor according to an illustrative embodiment of the invention.

Next, electrical impedance tomography (EIT) of the tumor together with the surrounding area is carried out by conventional means. As is well known, Standard EIT is carried out by applying an alternating electric field of selected frequencies to the body in the relevant area by appropriate electrodes while measuring the surface potential distribution by means of additional electrodes. On the basis of this information a 3D image of the impedance of the selected area is constructed, as illustrated in FIG. 3. This type of procedure is normally done in order to determine whether there is a tumor (characterized by an area with impedance that is different from the normal surroundings) in the scanned area. When this measurement is carried out within the framework of the "Inverse Electric Impedance Tomography" the standard alternating field/current frequency is replaced by one that is best suited for cell size determination.

It is important to note that EIS/EIT produces an impedance map of an object based upon the spatial electrical characteristics throughout the volume of the object. When a current is injected into an object, by Ohm's law the voltage drop will be proportional to the impedance of the object as long as the object has passive electrical characteristics. In EIS, a known current is injected into the surface and the voltage is measured at a number of points (electrodes) on the surface of the object. The resolution of the resultant image is dependent on the number of electrodes. Areas of low impedance typically appear on an EIS map as areas that have greater intensity (whiter). A measure of the electrical properties of the volume within the surface is obtained from these maps. An example of a device designed to detect tumors by EIT is the Siemens TS2000.

Figure 4:
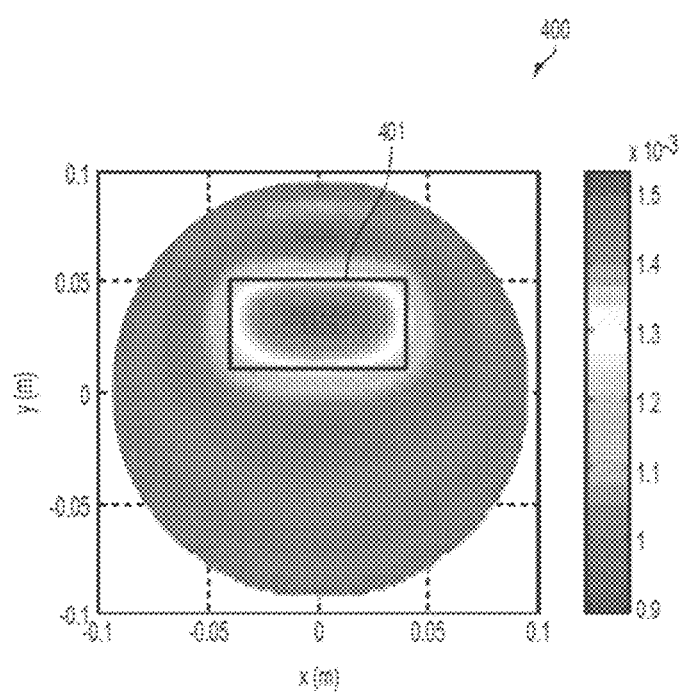
FIG. 4 is an image of a tumor and surrounding tissue according to an illustrative embodiment of the invention.

In this embodiment, an "inverse process" is being carried out as follows: In stage one above the existence and location of the tumor have been established using CT, MRI, PET, etc. The tumor coordinates thus obtained are provided to the processor that constructs the EIT image so that it will provide the calculated the average impedance values at selected tumor area as depicted in FIG. 4.

The impedance values of the specific tumor areas are registered for comparison with subsequent values obtained at later times. Note that the impedance is a function of the alternating field frequency used in the EIT. The impedance of the selected tumor area is now converted to average cell size or a spectrum of cell sizes on the basis of the electric impedance vs. cell size curves or tables of the relevant tumor, if available, or otherwise, on the calculations based on a geometric or Prismatic Cell in a Cube (PCIC) model.

Figure 1:
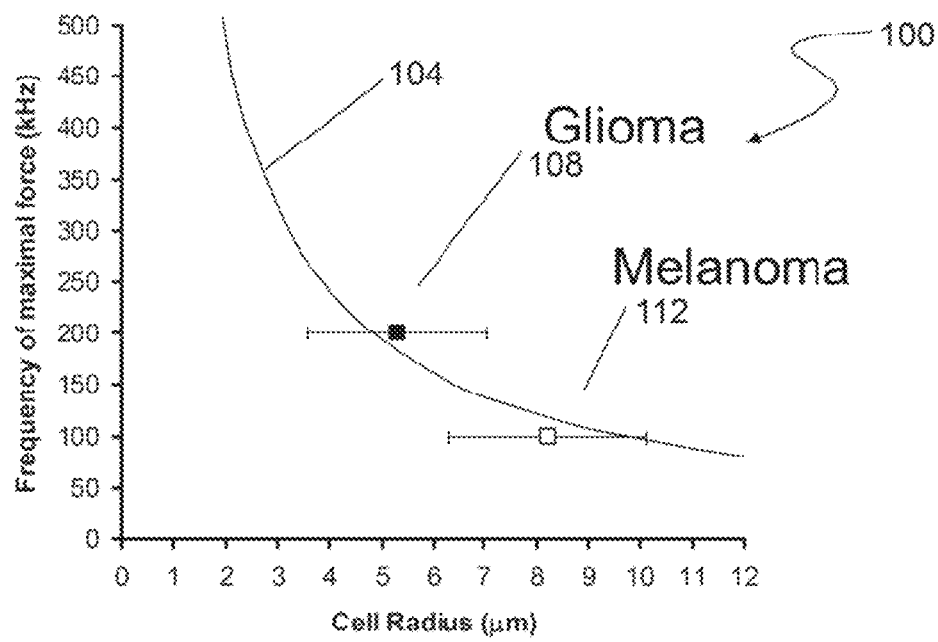
FIG. 1 is a graph of a calculated relationship between the cell radius and the optimal treatment frequency according to an illustrative embodiment of the invention.

FIG. 1 shows a graph 100 that includes a calculated relationship 104 between the cell radius (μm) and the optimal treatment frequency (kHz) as calculated on the basis of the maximal electric force exerted on the polar particles in the dividing tumor cell (during cytokinesis). FIG. 1 also shows experimentally determined treatment frequencies for glioma 108 and melanoma 112. Note that the experimentally determined optimal treatment frequencies and histological measurements of cell size in melanoma and glioma fall reasonably well on the calculated curve.

Figure 2:
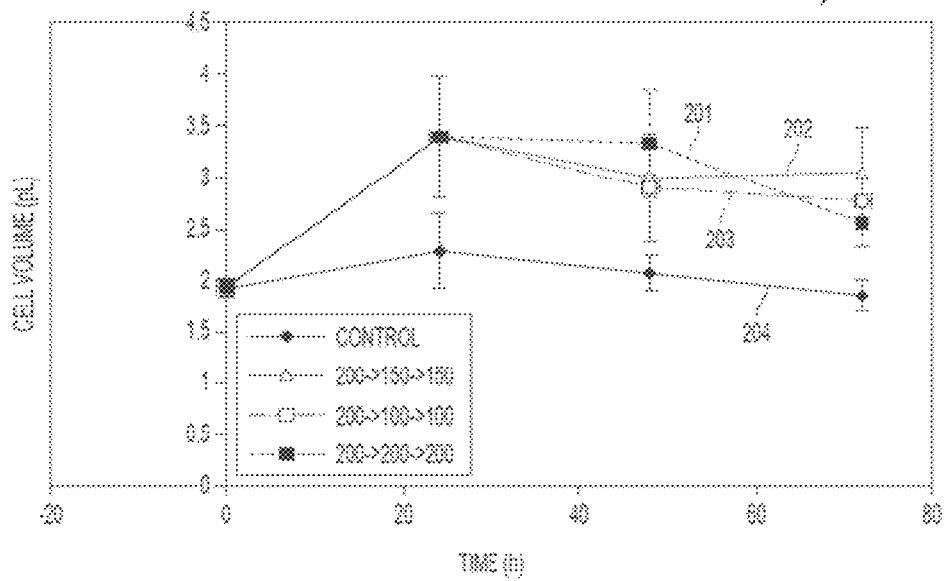
FIG. 2 is a graph showing cell volume in picoliters (pL) plotted against time in hours (h) according to an illustrative embodiment of the invention.

FIG. 2 shows a graph 200 of cell volume in picoliters (pL) plotted against time in hours (h). FIG. 2 illustrates how the cell size can change over time in a cell culture of A2780 human ovarian cancer cell line exposed to TTFields. It can be seen that in this case during the first 72 hours of treatment the cell volume increases. For example, FIG. 2 shows that for cells not exposed to TTFields (curve 204), the cell volume remains approximately constant, having a value of about 2 pL. Additionally, FIG. 2 shows that for cells exposed to TTFields (curves 201-203), the cell volume increase from a value of about 2 pL to a value of about 3 pL over the course of about 72 hours. Similarly, during long duration treatment in vivo, the cell volume changes may also differ. For example, in one patient who had three GBM biopsies over a period of two years of treatment with TTFields, histological sections indicated a 30% decrease in cell volume. In view of these volume changes with time, a frequency adjustment procedure is preferably repeated during the course of treatment (e.g., every few weeks or months), preferably depending on the type of tumor and the history of the tumor in the specific patient.

FIG. 3 shows an image 300 of a normal breast 304 and an image of a breast with a tumor 308. The images 304 and 308 can be acquired by x-ray, computed tomography (CT), magnetic resonance imaging (MM), positron emission tomography (PET), or equivalent. The breast tumor 312 appears as a white patch within image 308. The image 308 shows the shape, size, type, and location of the tumor 312.

FIG. 4 is a graph 400 of an electric impedance tomography (EIT) image of a tumor together with the surrounding areas, showing the electrical conductivity (S/m) of the imaged region plotted against position (m). The tumor is located in the rectangular region 404 of the graph.

Figure 5:
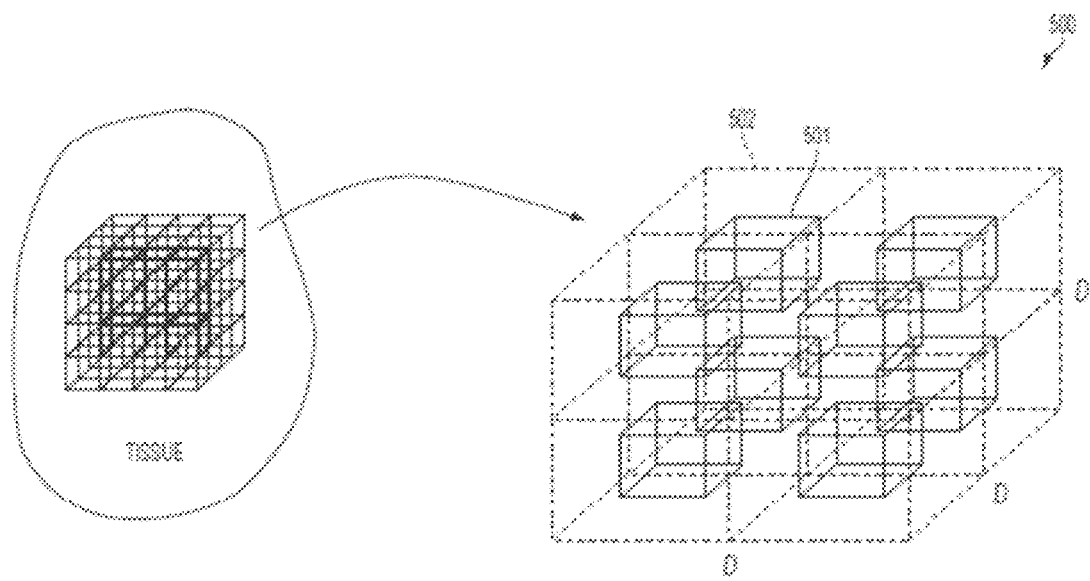
FIG. 5 is an image showing a geometrical model representation for cells in a tissue according to an illustrative embodiment of the invention.

FIG. 5 shows a geometrical model representation 500 for cells in a tissue. Following Gimsa (A unified resistor-capacitor model for impedance, dielectrophoresis, electro-rotation, and induced transmembrane potential. Gimsa J, Wachner D. Biophys J. 1998 August; 75(2): 1107-16.), the tissue can be modeled as elementary cubes 504, in which each elementary cube 504 is embedded with an elementary cell of prismatic geometry 508. The model representation 500 can be referred to as a prismatic cell in a cube model (PCIC). The geometrical model 500 can be mirror symmetric on the mid-plane of the cube.

Figure 6:
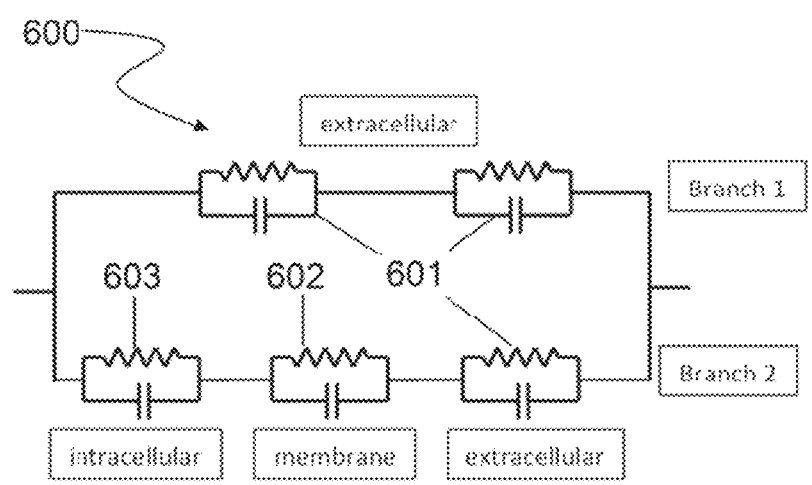
FIG. 6 is a diagram showing an RC circuit equivalent of a PCIC model according to an illustrative embodiment of the invention.

FIG. 6 shows an RC circuit 600 (i.e. a circuit containing resistors and capacitors) equivalent of a PCIC model, corresponding to one half of the prismatic cell in a cube. For a homogeneous medium, i, which contains the following tissue/cell elements: intracellular medium, extracellular medium and outer cell membrane, the impedance is modeled as a parallel RC circuit with a corresponding impedance (FIG. 6):

$$Z_i = \frac{L_i}{\sigma_i^* A_i}$$

where, $L_i$, $A_1$, and $\sigma_i^*$ are the length in parallel to the current, the area perpendicular to the current and the complex conductivity of medium i, respectively.

The complex conductivity can be modeled as:

$$\sigma_i^* = \sigma_i + j\omega\varepsilon_i\varepsilon_o$$

The equivalent RC circuit can be used to model a homogeneous medium that contains an intracellular medium 603, extracellular medium 601, and outer cell membrane 602. In cases where the geometrical model is mirror symmetric on the mid-plane of the cube, such as is shown in FIG. 5, the impedance of only one half of the equivalent circuit needs to be solved and the total impedance is just twice the calculated one.

Figure 7:
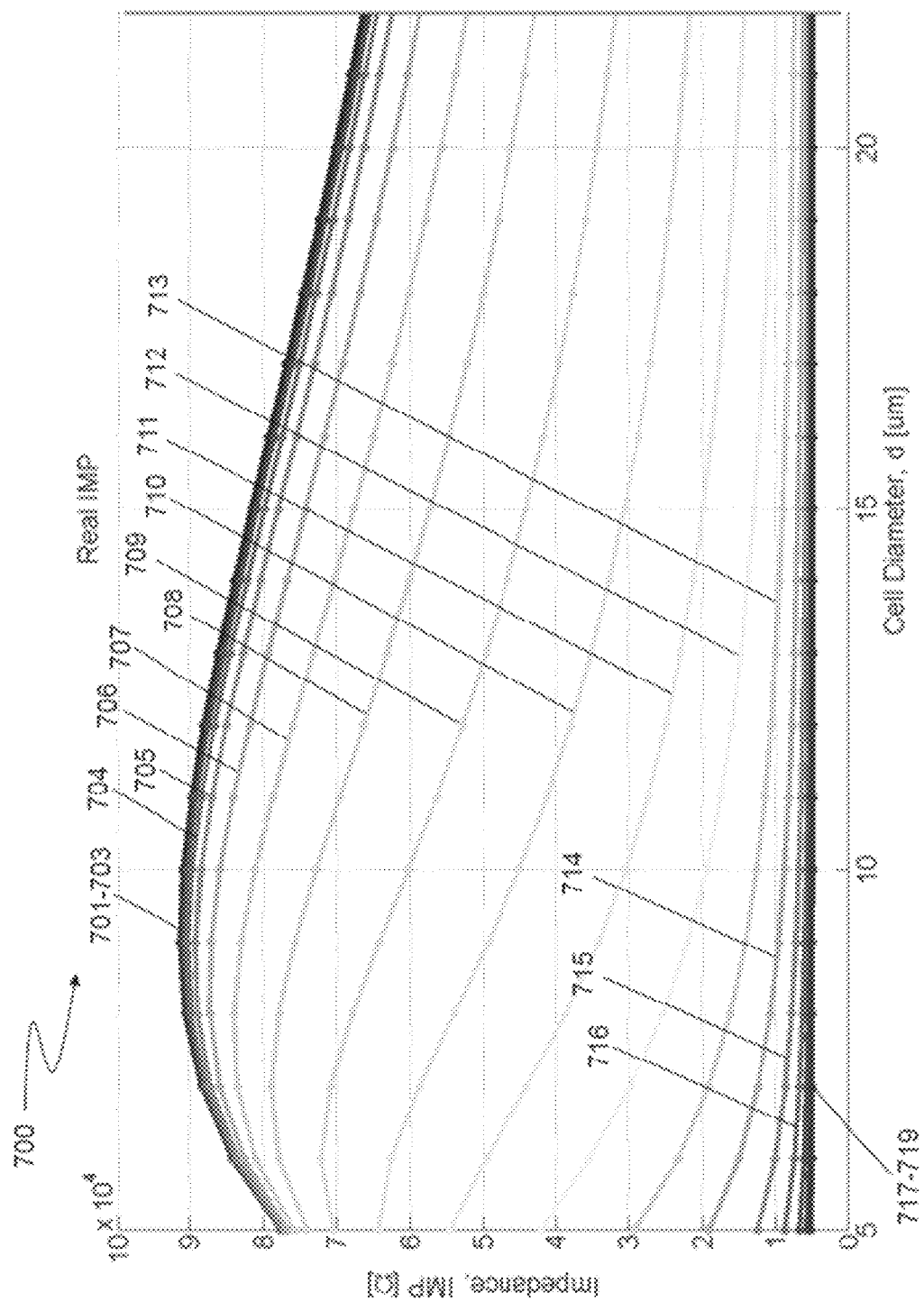
FIG. 7 is a graph showing the real part of the impedance plotted against cell diameter for a variety of different frequencies according to an illustrative embodiment of the invention.
Figure 8:
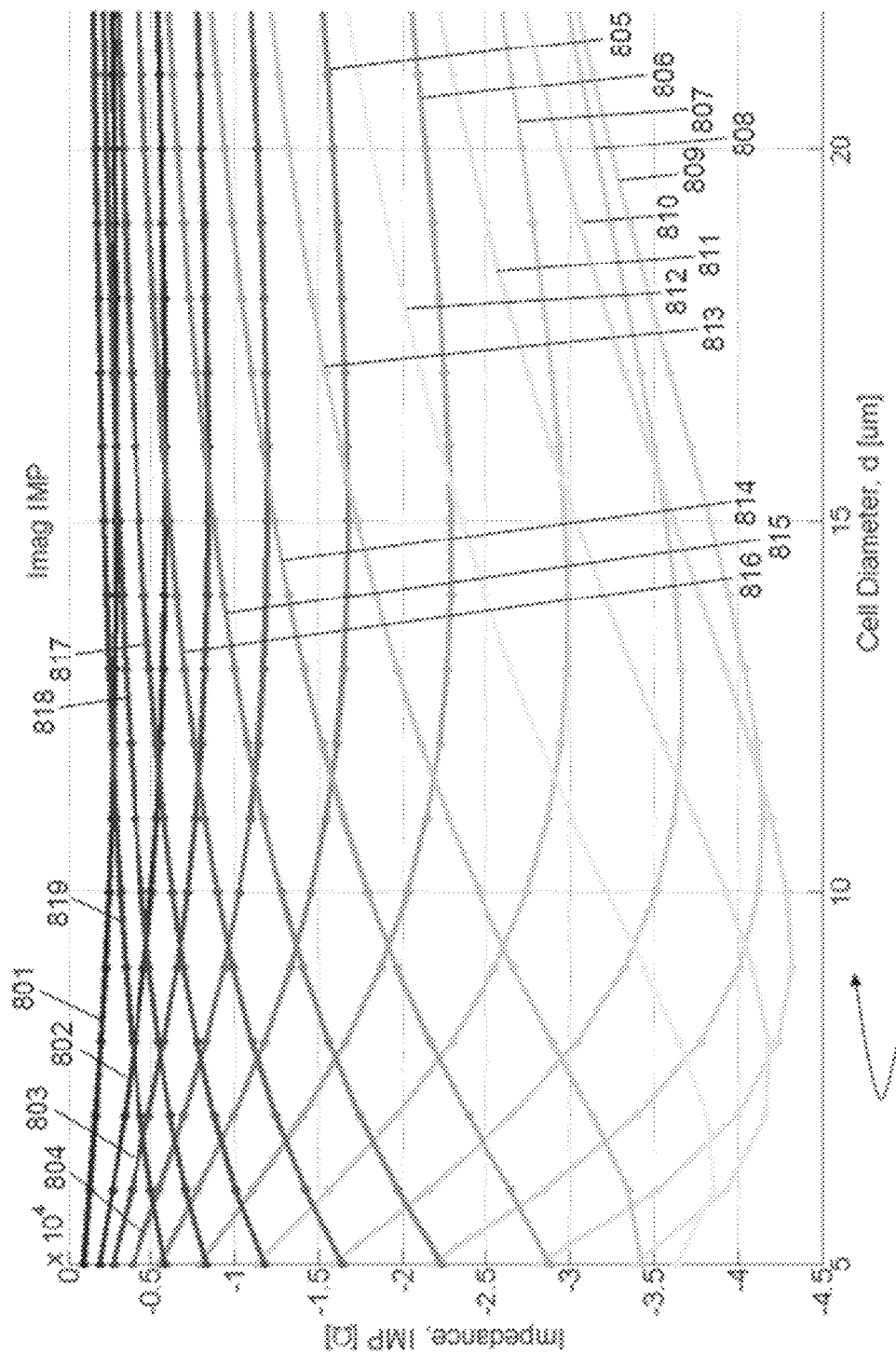
FIG. 8 is a graph showing the real part of the impedance plotted against cell diameter for a variety of different frequencies according to an illustrative embodiment of the invention.
Figure 9:
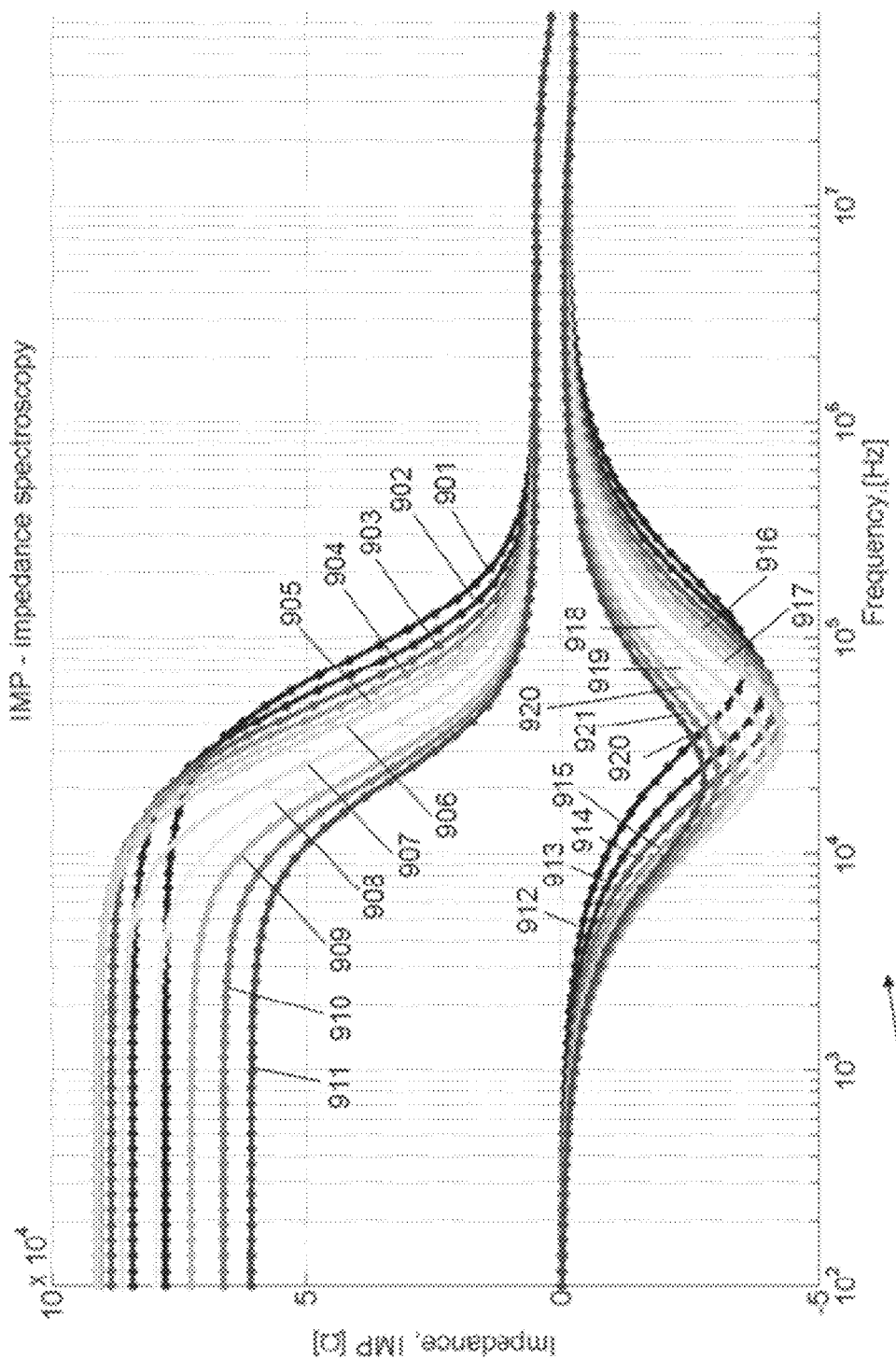
FIG. 9 is a graph showing the real and imaginary parts of the impedance plotted against frequency for a variety of different cell diameters according to an illustrative embodiment of the invention.
Figure 10:
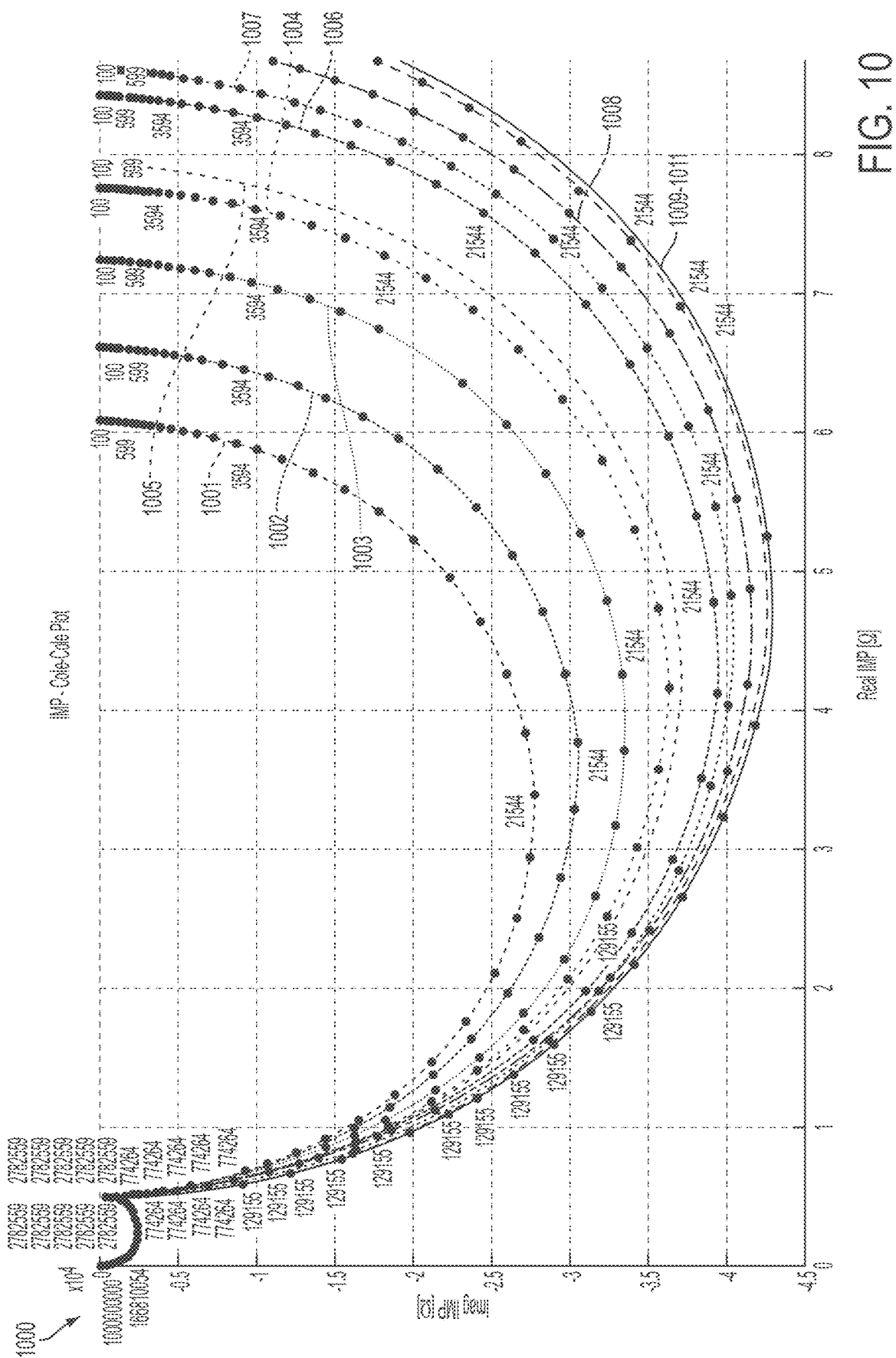
FIG. 10 is a graph showing a Cole-Cole plot according to an illustrative embodiment of the invention.

FIGS. 7-9 show graphs of the real and imaginary parts of the impedance as a function of cell diameter of the constituent cells for a range of electromagnetic frequencies between 1 kHz and 1 MHz used during the impedance measurement. FIG. 7 shows a graph 700 of the real component of impedance plotted against cell diameter for a variety of electromagnetic frequencies. For example, curves 701, 702, 703, 704, 705, 706, 707, 708, 709, 710, 711, 712, 713, 714, 715, 716, 717, 718, and 719 correspond to electromagnetic frequencies of 1 kHz, 2 kHz, 3 kHz, 4 kHz, 6 kHz, 9 kHz, 13 kHz, 18 kHz, 26 kHz, 38 kHz, 55 kHz, 78 kHz, 113 kHz, 162 kHz, 234 kHz, 336 kHz, 483 kHz, 695 kHz, and 1000 kHz, respectively. FIG. 8 shows a graph 800 of the imaginary component of impedance plotted against cell diameter for a variety of electromagnetic frequencies. For example, curves 801, 802, 803, 804, 805, 806, 807, 808, 809, 810, 811, 812, 813, 814, 815, 816, 817, 818, and 819 correspond to electromagnetic frequencies of 1 kHz, 2 kHz, 3 kHz, 4 kHz, 6 kHz, 9 kHz, 13 kHz, 18 kHz, 26 kHz, 38 kHz, 55 kHz, 78 kHz, 113 kHz, 162 kHz, 234 kHz, 336 kHz, 483 kHz, 695 kHz, and 1000 kHz, respectively. FIG. 9 shows a graph 900 of both the real and imaginary parts of the impedance plotted against frequency different cell diameters of constituent cells. For example, curves 901, 902, 903, 904, 905, 906, 907, 908, 909, 910, and 911 correspond to the real part of the impedance for cell diameters of 5 μm, 6 μm, 7 μm, 8 μm, 9 μm, 10 μm, 13 μm, 16 μm, 19 μm, 22 μm, and 25 μm, respectively. Additionally, curves 912, 913, 914, 915, 916, 917, 918, 919, 920, 921, and 922 correspond to the imaginary part of the impedance for cell diameters of 5 μm, 6 μm, 7 μm, 8 μm, 9 μm, 10 μm, 13 μm, 16 μm, 19 μm, 22 μm, and 25 μm, respectively. FIG. 10 shows a graph 1000 of the real part of the impedance plotted against the imaginary part of the impedance for a variety of different cell diameters of constituent cells. For example, curves 1001, 1002, 1003, 1004, 1005, 1006, 1007, 1008, 1009, 1010, and 1011 correspond to cell diameters of 5 μm, 6 μm, 7 μm, 8 μm, 9 μm, 10 μm, 13 μm, 16 μm, 19 μm, 22 μm, and 25 μm respectively. The curves 1001-1011 further contain information about the electromagnetic frequency applied to the constituent cells. From right to left, the frequency increases along the clockwise direction of the curve from about 100 Hz on the far right, to about 1 MHz on the far left. A Cole-Cole plot as shown in FIG. 10 can be constructed based on the data shown in FIGS. 7-9.

Once the impedance of the tumor is known, FIGS. 7-9 can be used to infer the cell size. The impedance of an array of PCIC blocks, i.e. the IMP, can be easily deduced from the impedance of one PCIC block, the imp, through:

$$IMP = \frac{\left(\frac{D}{a}\right)}{\left(\frac{D}{a}\right)^2} imp = \frac{a}{D} imp$$

where D is the side length of a cube of the tissue (or tumor) and a is the side length of the PCIC block. It is important to note that FIGS. 7-9 indicate that there are preferable frequencies that should be used in the impedance tomography. As seen, for example, in FIG. 7 up to frequencies of about 30 kHz the impedance (real component) vs. cell size curves have a peak, i.e. there are cell sizes with the same impedance (two relevant solutions to the equations) leaving an ambiguity as to the actual size. However, for higher frequencies the curves are monotonous and there is a unique solution/size corresponding to each impedance value. Thus the impedance tomography should preferably be performed at frequencies that provide unique cell sizes. Once the cell size is determined, the optimal treatment frequency can be determined on the basis of curves such as those depicted in FIG. 1. Note that for the calculations presented in FIGS. 7-9, the elementary cube of tissue (or tumor) is chosen to have a size of 1 mm. Other parameters used in the calculations shown in FIG. 7-9 can be found in Table 1 as shown in FIG. 13. In alternative embodiments, the data from FIG. 10 can be used to infer the cell size once the impedance has been determined.

Note that viewing the data from FIG. 10 and FIG. 1 together leads to the conclusion that a direct relationship exists between measured impedance and the desirable treatment frequency, such that the treatment frequency can be determined directly from the measured impedance.

FIG. 10 shows a Cole-Cole plot that can be used to determine the size of a cell based on an impedance measurement. The Cole-Cole plot shows the impedance spectrum of the constituent cells as a function of the cell diameter. Note that in cases where both the tumor cell size, area of necrosis, cyst or level of vascularization change with time a potential error may be introduced by the impedance changes resulting from the changes in fluid or blood volume within the tumor. This can be corrected for along two pathways. When the fluid (blood, cyst fluid) volume is large enough, it can be detected by the CT and the impedance tomography images and thus non affected areas can be selected for the computation. Alternatively corrections can be made on the basis of the fact that the cell membranes of the cell mass have both capacitive and resistive i.e. real & imaginary components while the fluids and blood are, to a good approximation, primarily resistive elements. Here the correction is based on the construction of a Cole-Cole plot (see the example given in FIG. 10) from the tumor impedance values as determined by impedance tomography. In our case, these measurements are carried out at frequencies in the range dictated by the requirements of the Cole-Cole plot for tissue rather than by the optimal frequency requirements of impedance tomography. Note that the changes in the blood content of the tumor will be reflected mainly in the resistive aspect of the Cole-Cole plot. Utilizing the ratio between the impedance of the tumor and the tissue surrounding the tumor may add to the accuracy.

Figure 11:
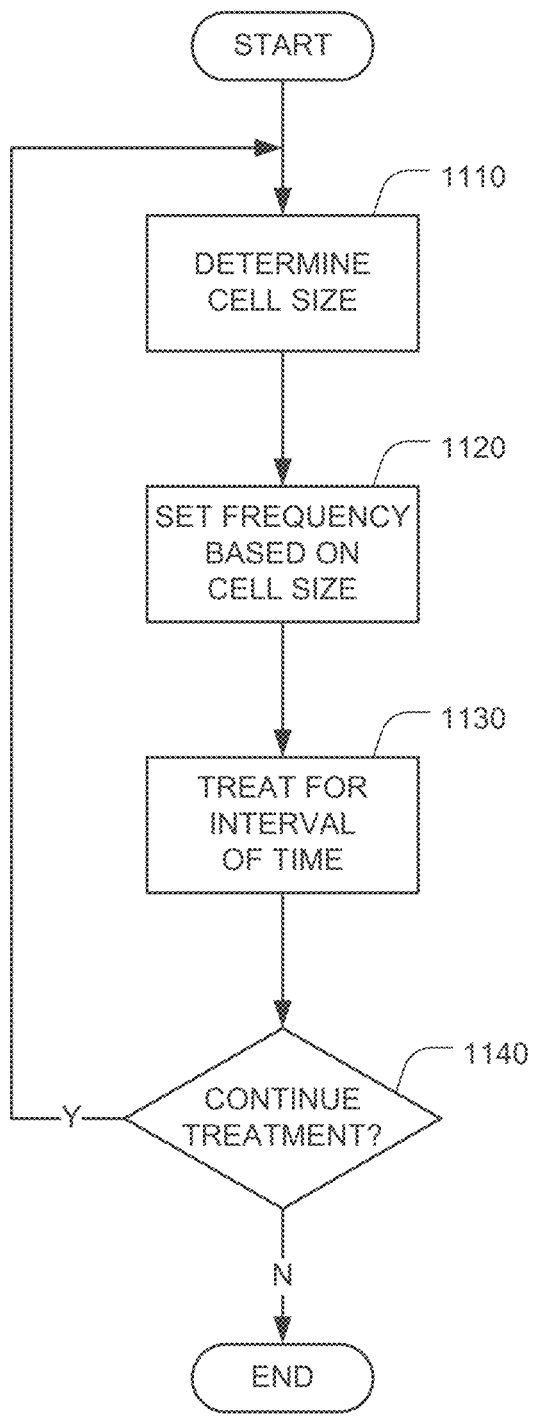
FIG. 11 is a flow chart illustrating a method in accordance with one embodiment for adjustment the treatment frequency during the course of tumor treatment in accordance with an illustrative embodiment of the invention.

FIG. 11 shows a method for adaptively treating a tumor with electromagnetic radiation. The method includes determining a cell size (step 1110). The cell size can be determined by first locating the tumor by a conventional imaging method, such as CT, Mill, or PET. The cell size can also be determined from histological sections made of samples obtained by biopsies of the tumor taken from the specific patient. The cell size can also be predicted based on the type of cancer involved. After locating the tumor, inverse electrical impedance tomography (IEIT) of the tumor together with the surrounding area can be performed. As is well known, Standard EIT is carried out by applying an alternating electric field of selected frequencies to the body in the relevant area by appropriate electrodes while measuring the surface potential distribution by means of additional electrodes.

On the basis of this information a 3D image of the impedance of the selected area is constructed, as illustrated in FIG. 4. This type of procedure is normally done in order to determine whether there is a tumor (characterized by an area with impedance that is different from the normal surroundings) in the scanned area. When this measurement is carried out within the framework of the IEIT, the standard alternating field/current frequency is replaced by one that is best suited for cell size determination. FIGS. 7-10 show exemplary frequencies suitable for carrying out IEIT.

For example, referring to FIG. 7, a frequency of 38 kHz (corresponding to curve 711) may be preferable when determining cell size via IEIT. The method also includes setting a frequency based on the determined cell size (step 1120). The frequency can be selected on the basis of curves such as those depicted in FIG. 1. The treatment frequency adjustment preferably occurs before the initialization of treatment and according to this embodiment readjustment continues during the treatment, the duration of which may be months and even years. The method also includes treating the tumor for an interval of time (step 1130), using the new treatment frequency. In some embodiments, the treatment frequency can include two or more frequencies that can be applied to the tumor either sequentially or simultaneously. The initial setting of the frequency is preferably selected by first determining or estimating the average size of the tumor cell and spectrum of cell sizes in step 1110.

In a particular embodiment, three frequencies are provided in an interleaved fashion, such that first frequency F1 is applied for a period of time, then second frequency F2 is applied for a period of time, and then third frequency F3 is applied for a period of time. Then the cycle repeats, starting again with F1. The duration of each time period can be different for each frequency, but in an embodiment the time periods are the same. This treatment allows simultaneous treatment of different types of tumors, or treating a tumor with different cell sizes.

The initial size is preferably determined from histological sections made of samples obtained by biopsies of the tumor taken from the specific patient. But it can also be set using a prediction that is based on the type of cancer or using the impedance approach described in relation to FIGS. 7-9. After a suitable interval of time has elapsed (e.g., a few weeks or months), a decision to continue treatment is made (step 1140). If the treatment is to be continued, processing returns to step 1110, where the next cell size determination is made. Otherwise, the treatment adjustment ends. The tumor cell size is preferably evaluated periodically, e.g., every 1-3 months, preferably using one or more of the following three approaches: (1) tumor biopsies, (2) the novel algorithms described herein that relate the cell size to the patient's tumor impedance as determined by special procedures, or (3) a data base look-up table. If the cell size has changed, the treating field frequency is adjusted accordingly in step 1120. The new treatment frequency is then used in step 1130.

Figure 12:
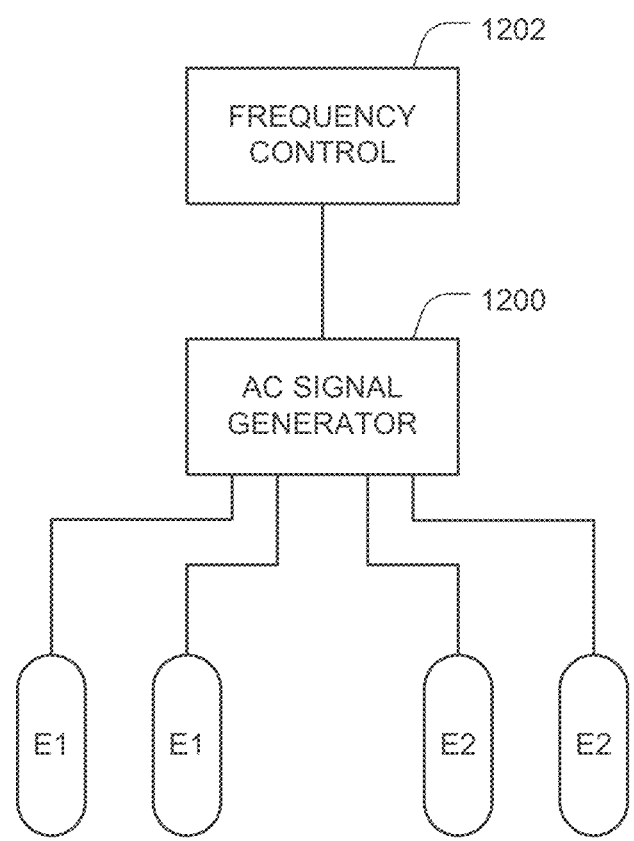
FIG. 12 is a diagram of an apparatus for adjusting the treatment frequency of a tumor during the course of treatment according to an illustrative embodiment of the invention.

FIG. 12 is a block diagram of a system that can apply TTFields with the different frequencies to the patient. The core of the system is an AC signal generator 1200 whose output is hooked up to at least one pair of electrodes E1. Preferably, at least one additional pair of electrodes E2 is also hooked up to additional outputs of the signal generator. The signals are preferably applied to the different pairs of electrodes sequentially in order to switch the direction of the electric field, as described in U.S. Pat. No. 7,805,201.

The AC signal generator 1200 has a control that changes the frequency of the signals that are generated. In some embodiments, this control can be as simple as a knob that is built in to the signal generator. But more preferably, the AC signal generator 1200 is designed to respond to a signal that arrives on a control input, and the frequency control 1202 sends a suitable signal (e.g., an analog or digital signal) to the control input of the AC signal generator 1200 to command the signal generator to generate an output at the desired frequency. The frequency control 1202 can send a frequency to the AC signal generator 1200 based on a measured or estimated cell diameter. The cell diameter can be determined by a histological measurement or by IEIT.

Once the cell diameter is determined, an optimal treatment frequency can be determined. The frequency control 1202 can then send a control signal to the AC signal generator 1200 to set the frequency of the AC signal generator to the optimal treatment frequency. A processor can be coupled to the frequency control 1202 to automate the process of selecting an optimal treatment frequency based on a measured or estimated cell diameter. The processor can receive information about the measured or estimated cell size and then determine an optimal treatment frequency based on the received information. After determining an optimal treatment frequency, the processor can send a control signal to the frequency control 1202 that causes the frequency control 1202 to send a signal the AC signal generator 1200 that causes the AC signal generator to output the optimal treatment frequency.

While the embodiments described thus far have been focused on adaptively treating a tumor with TTFields, the invention has broader implications. In various embodiments, IEIT could be used to measure the impedance of a group of patient cells. The determined impedance of the group of patient cells could then be used to adjust a parameter of the treatment. The treatment could be a surgery or a therapy such as chemotherapy, radiation therapy, pharmacotherapy, or nutritional therapy. In some embodiments, the determined impedance of the patient cells can be used to estimate the size of cells in the group of patient cells. A parameter of the treatment could then be adjusted based on the estimated cell size.

The terminology used herein is for the purpose of describing particular embodiments and is not intended to be limiting of the inventive concepts. It will be understood that, although the terms first, second, third etc. are used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present application.

While the present inventive concepts have been particularly shown and described above with reference to exemplary embodiments thereof, it will be understood by those of ordinary skill in the art, that various changes in form and detail can be made without departing from the spirit and scope of the present inventive concepts described and defined by the following claims.

What is claimed is:

1. An apparatus for adaptively treating a tumor with an alternating electric field, the apparatus comprising:
    an AC signal generator having an output;
    at least one pair of electrodes operatively connected to the output of the AC signal generator such that an alternating electric field is applied to the tumor to selectively destroy cells in the tumor, wherein the AC signal generator is configured to apply a first alternating electrical signal to the output for a first period of time;
    an electrical impedance tomography device for measuring an impedance of the tumor to account for expected changes that occur as a result of treating the tumor for the first period of time; and
    a processor configured to adjust an operating frequency of the AC signal generator based on the measured impedance of the tumor after the first period of time, and further configured to account for changes in the tumor that have occurred during the first period of time by controlling the AC signal generator so that the AC signal generator applies a second alternating electrical signal to the output for a second period of time using the adjusted operating frequency,
    wherein the second period of time is subsequent to the first period of time.

2. The apparatus of claim 1, wherein the first alternating electrical signal has a first frequency, and wherein the second alternating electric signal has a second frequency that is different from the first frequency.

3. The apparatus of claim 1, wherein the AC signal generator and the electrical impedance tomography device are separate devices.

4. A method for adaptively treating a tumor with an alternating electric field, the method comprising:
    applying a first alternating electric field to the tumor for a first period of time to selectively destroy cells in the tumor;
    measuring an impedance of the tumor to account for expected changes that occur as a result of treating the tumor for the first period of time;
    adjusting an operating frequency of treatment based on the measured impedance of the tumor after the first period of time to account for changes in the tumor that have occurred during the first period of time; and
    applying a second alternating electric field to the tumor for a second period of time to selectively destroy cells in the tumor, wherein the second alternating electric field uses the adjusted operating frequency,
    wherein the second period of time is subsequent to the first period of time.

5. The method of claim 4, wherein the first alternating electrical field has a first frequency, and wherein the second alternating electric field has a second frequency that is different from the first frequency.

* * * * *